US005191903A

United States Patent [19]

Donohue

[11] Patent Number: 5,191,903

[45] Date of Patent: Mar. 9, 1993

[54] DIGITAL TRACTION SYSTEM

[76] Inventor: Patrick T. Donohue, 1822 N.E. 143rd, Portland, Oreg. 97230

[21] Appl. No.: 711,916

[22] Filed: Jun. 6, 1991

[51] Int. Cl.[5] .................... A61F 5/04

[52] U.S. Cl. .................... 128/879; 602/5; 602/21; 602/22

[58] Field of Search .................... 128/83, 84 R, 84 B, 128/84 C, 846, 87 B, 879, 165; 602/53, 60, 62, 65, 66, 72, 73, 105

[56] References Cited

U.S. PATENT DOCUMENTS

| | | | |
|---|---|---|---|
| Re. 33,182 | 3/1990 | Pecheux | 128/77 X |
| 2,237,251 | 12/1938 | Longfellow | 128/87 |
| 2,438,144 | 3/1948 | Bunyar, Jr. | 128/77 UX |
| 2,646,794 | 7/1953 | Baer | 128/85 |
| 3,872,861 | 3/1975 | Tamney et al. | 128/84 R |
| 4,602,620 | 7/1986 | Marx | 128/84 C X |
| 4,719,906 | 1/1988 | Deprospero | 128/77 X |
| 4,741,087 | 5/1988 | Plummer, Jr. | 29/446 |
| 4,945,902 | 8/1990 | Dorer | 128/87 |
| 4,949,711 | 8/1990 | Gyovai et al. | 128/77 X |
| 5,027,802 | 7/1991 | Donohue | 128/77 X |

FOREIGN PATENT DOCUMENTS

| | | |
|---|---|---|
| 589416 | 6/1947 | United Kingdom . |
| 650952 | 4/1949 | United Kingdom . |

OTHER PUBLICATIONS

"1989 Orthopedics" catalog, p. B19, Fred Sammons, Inc., Burr Ridge, Ill., 1989.

*Primary Examiner*—Robert A. Hafer
*Assistant Examiner*—Sam Rimell
*Attorney, Agent, or Firm*—Bruce J. Ffitch

[57] ABSTRACT

An axial digital traction system is disclosed in a hand application. A traction plate is anchored close to the base of the fingers or metacarpophalangeal joints by a hook and loop type fabric fastener, such as that sold under the trademark "VELCRO" connecting the traction plate to a fingerless glove-like anchoring member worn by the patient. Tension elements fastened to the traction plate are trained over rollers at the end of the plate and connected to finger traps which grip the patient's fingers. An alternative traction plate arrangement facilitates treatment of individual digits and provides for greater range of independent articulation of an mcp joint while under treatment.

17 Claims, 2 Drawing Sheets

FIG. 4
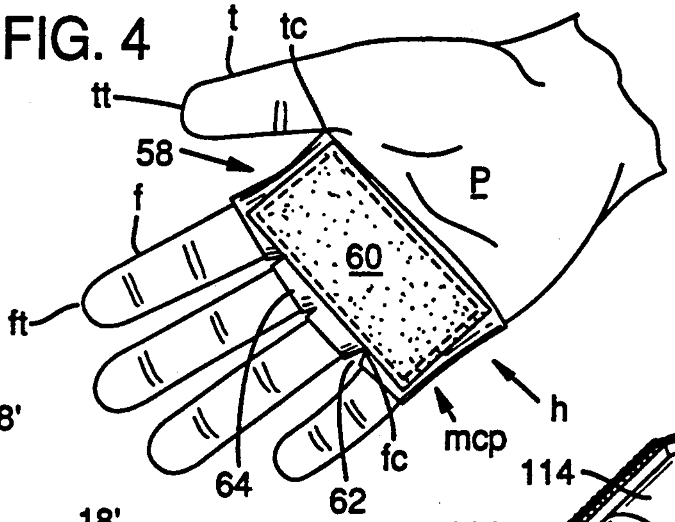
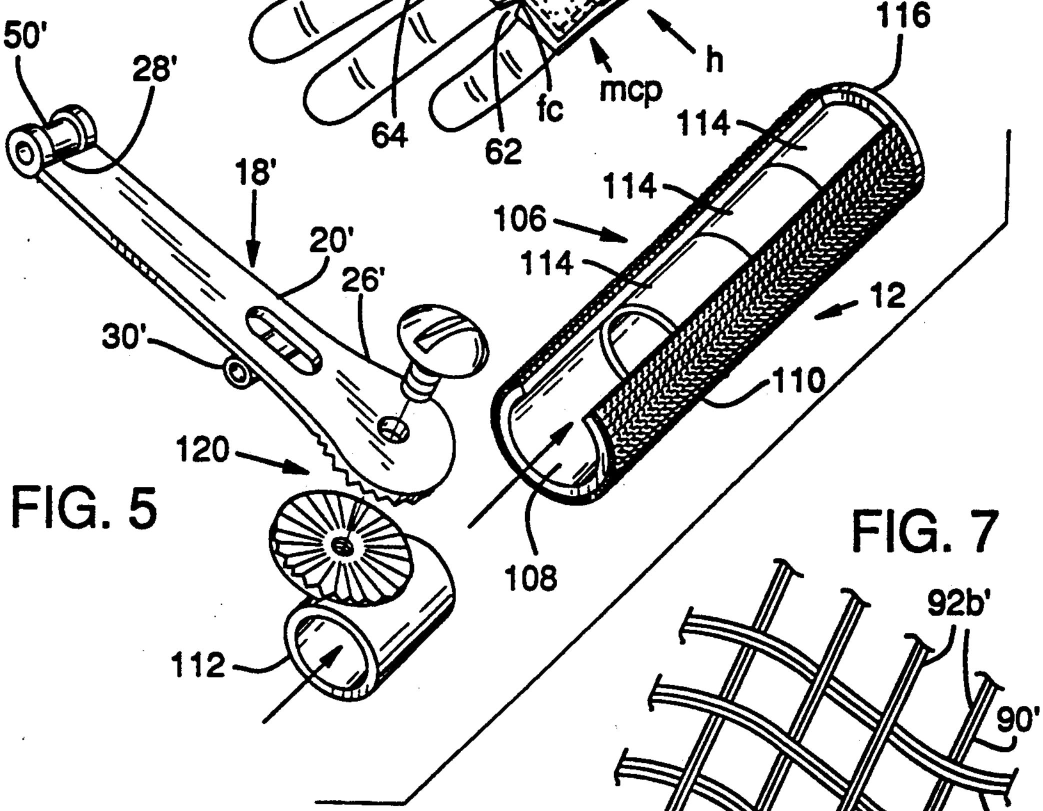
FIG. 5
FIG. 7
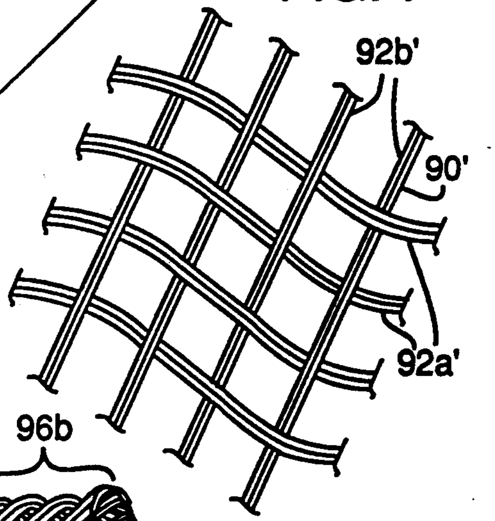
FIG. 6
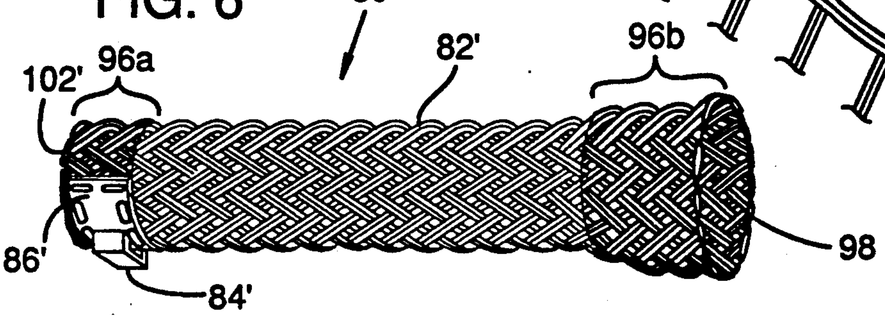

DIGITAL TRACTION SYSTEM

BACKGROUND OF THE INVENTION

The invention concerns devices for applying therapeutic traction to the digits of the extremities (hands or feet) and, more particularly, to devices which are self-contained, thus maintaining patient mobility.

Traction systems and devices according to the invention may be applied to the digits of both hands and feet but for convenience the following discussion will be limited to the hand application.

Traction is indicated and potentially beneficial for a number of health conditions, including arthritis, and many devices are available.

Certain non-malignant conditions, such as arthritis, repetitive motion injury, trauma and the like, cause unnatural pull on the muscles, tendons and ligaments of the hand resulting in painful joints, deformities and sometimes partial or total loss of use of the hand. Pain, loss of joint strength and range of motion may be experienced because a phalanx drifts or is pulled out of its normal position in relation to another phalanx or the metacarpal bone, causing the respective joint to become deformed. Or the phalanges and metacarpals of the hand may partially degenerate as a result of disease and the like, resulting in deformities (misalignment) or distortions of the hand.

Devices which apply an axial force (traction) across a joint tend to:

1) Lower the pressure within the joint, resulting in pain relief and an increase in localized blood circulation.

2) Strengthen the muscles, tendons, and ligaments.

3) Restore the joint's normal range of motion.

4) Act as an opposing force to undesirable joint contractive forces which can cause deformities.

5) Facilitate the healing process.

Application of a static tensile force to a digit requires, of course, a tension member which is fixed at both ends, one end connected to the digit and the other end anchored at a point fixed in relation to the point of attachment to the digit. In some devices this anchor or reaction point of the tension member may be remote from the hand on another part of the body or for example on the frame of a bed supporting the patient. In devices which may be classed broadly as self-contained the anchor point is on the hand and/or wrist. Self-contained devices are potentially more compact and provide greater mobility for the patient.

The present invention is related to the self-contained group. Known devices in this class tend to be complex, requiring skilled application and custom fitting as well as being heavy and clumsy, offering serious hindrance to the patient's mobility and normal activities. Commonly the ultimate anchoring point is the wrist or forearm so that the whole hand and the wrist itself are encumbered by the traction device. See for example British patents 589,416 Meyer and 620,952 Bolliger and U.S. Pat. No. 4,945,902 Dorer.

SUMMARY OF THE INVENTION

Accordingly, it is an object of the invention to provide a simple low cost digital traction system capable of applying axial traction to all joints of a digit including the metacarpophalangeal joint and, optionally, to all digits of the hand (or foot) and lending itself to mounting, adjustment and management by the patient with a minimum of medical intervention.

In one form, the invention may comprise a traction system for applying traction to at least one of the metacarpophalangeal joints of a hand, the hand having a plurality of digits and crotches between the digits, the system including a traction frame for anchoring alongside the hand and means connectable between at least one digit and the frame for applying a traction force through the digit to the corresponding metacarpophalangeal joint and characterized in that the system includes a glove-like anchoring member embracing and covering at least part of the hand in a substantially fixed relationship with the hand and in that the traction frame is anchored to the hand by means of the anchoring member and so that, in use, retraction of the traction frame under the action of the traction force applying means is resisted substantially by the engagement of the anchoring member with the hand.

It is also an object to provide a digital traction device which is light in weight and of low profile so as to offer minimum impedance to the mobility and activity of the patient. Preferably the device permits some use of the patient's hand in at least one mode of operation.

It is also an object to provide a digital traction system which is conveniently portable and which can be used satisfactorily for a wide range of hand sizes using a common set of components.

Another object of the invention is to provide a digital traction system which permits, selectively, application of traction to any combination of one or more digits or to all digits of the hand. All applications make use of a traction plate or plates which, preferably, are anchored at the palm of the hand adjacent the metacarpophalangeal (mcp) joints and hence adjacent the base of the digit or digits to be treated.

These objects may also be realized in a digital traction system based on one or more traction plates which share a common profile but are of different widths. In use they may normally lie, generally parallel to the digits being treated, inside the hand (palmar position), and span the length of the digits from near their base to a point adjacent to but preferably somewhat beyond the tips of the digits. Traction may be applied individually to each digit by a separate elongated tension member having one end connected to the traction plate, and preferably passing over the outer end of the plate and returning, for attachment of the opposite end of the tension member to the digit to be treated. It is desirable that, in operation, the tension member be at uniform tension over its entire length. Preferably a low friction surface such as a pulley or roller is provided at the outer end of the traction plate to facilitate this.

Clearly the arrangement just described results in the traction plate or frame being biased towards the base or root of the digits and palm of the hand, and the inner end of the plate must of course be anchored. In the embodiments disclosed here the traction plate or frame is disposed on the palmar side of the hand and is anchored by providing means for temporary adhesion of its inner end to the hand, closely adjacent the base of the fingers. In a preferred embodiment a temporary adhesion or releasable anchoring may be provided by using a glove-like anchoring member and providing self-connecting surfaces, such as hook and loop fabric fasteners (of the type, for example, sold under the trademark "VELCRO") on the registering and connecting portions of the traction plate and the anchoring member.

The anchoring member may be glove-like in that it bears on and partially conforms to at least part of the hand and includes a portion engageable with the crotches between the fingers.

The preferred embodiments may include the use of traction plates or frames of a common profile but of different widths, common tension members and also a particular adaptation of the well known Chinese finger trap as the input members for applying traction to the digit.

The sleeve of the finger trap may be of braided strand construction, each strand consisting of a plurality of filaments of a pliable material such as polypropylene or possibly polyethylene, bundled relatively loosely and in linear alignment for improved comfort (due to load spreading) and efficiency of the finger trap. In this adaptation, the outer or distal end of the finger trap is open so that, if desired, the finger tip may protrude through and the tension member may be attached to the body of the finger trap at a point somewhat inset from its outer end. This arrangement helps to minimize the length of the traction plate and potentially contributes to the overall compactness and lightness of devices according to the invention.

To provide versatility in application the range of traction plates or frames may include a full width plate providing for simultaneous application of traction to all five digits, or narrower plates including, for example, an individual digit plate. Preferably the anchoring of the single digit plate provides for lateral adjustment of its anchoring point relative to the hand. Single digit plates may also be pivotally adjustable s that the direction of the traction force may deviate from the axis of the digit.

Other features and advantages of a digital traction system according to the invention will become apparent from the description which follows.

BRIEF DESCRIPTION OF THE DRAWINGS

FIG. 4 is a palmar view similar to FIG. 2 but to a reduced scale and showing only the glove-like anchoring member carried by the hand.

FIG. 5 is a perspective exploded view of the second embodiment of traction plate assembly shown in assembly in FIG. 3 and including individual digit traction plates laterally adjustable within an anchor member and also pivotaly adjustable.

FIG. 6 is a perspective view of one of the finger trap components of the system.

FIG. 7 is an enlarged partial view showing the weave pattern of the fabric of the finger trap of FIG. 6.

DESCRIPTION OF THE PREFERRED EMBODIMENTS

Figure 1:
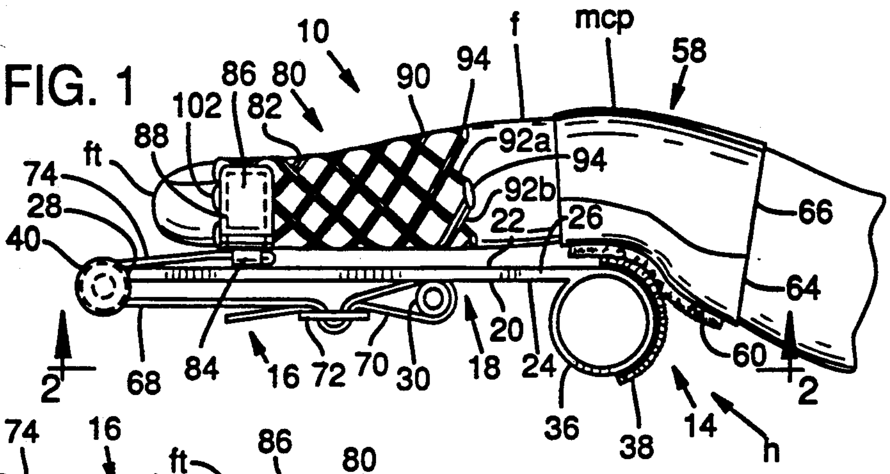
FIG. 1 is a side view of a digital traction system applied to a right hand with the traction producing elements mounted on the palmar side of the hand. For clarity the thumb is omitted from the drawing.
Figure 2:
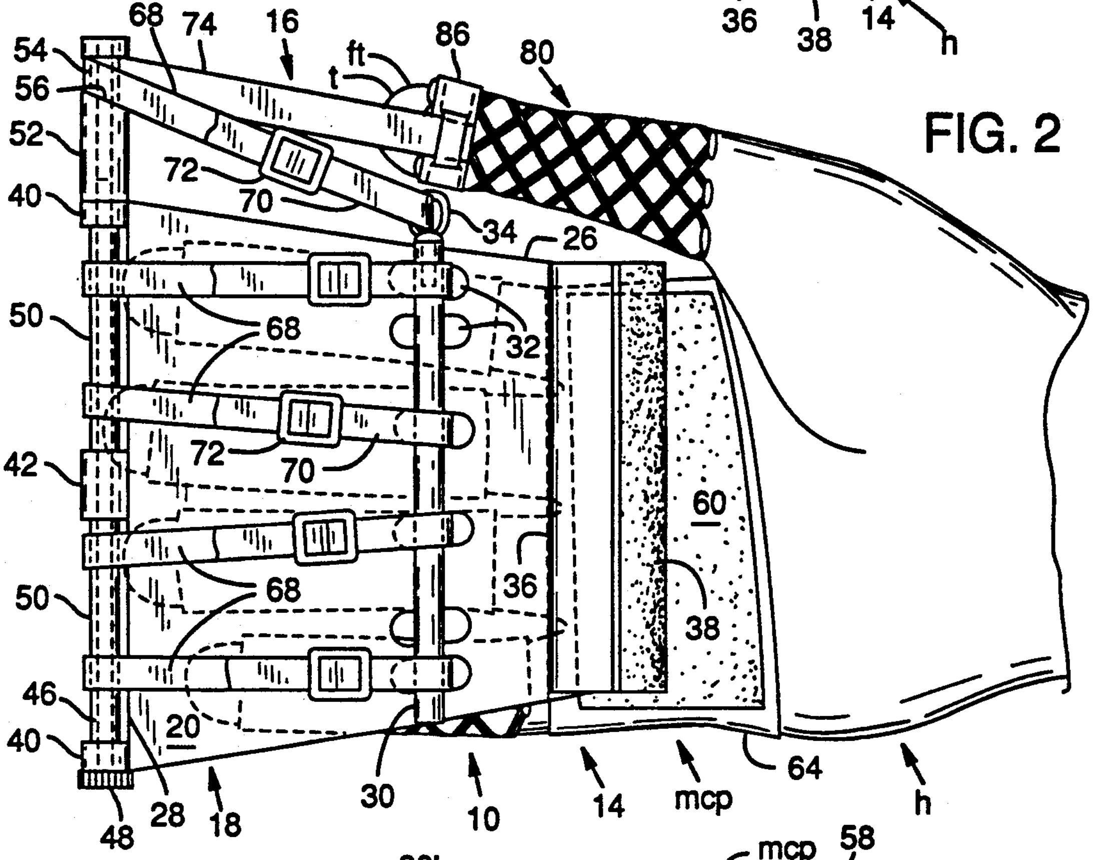
FIG. 2 is a palmar view taken approximately on line 2—2 of FIG. 1 but including the thumb.

The invention is embodied in the digital traction system 10 illustrated in a first embodiment, particularly in FIGS. 1 and 2.

Figure 3:
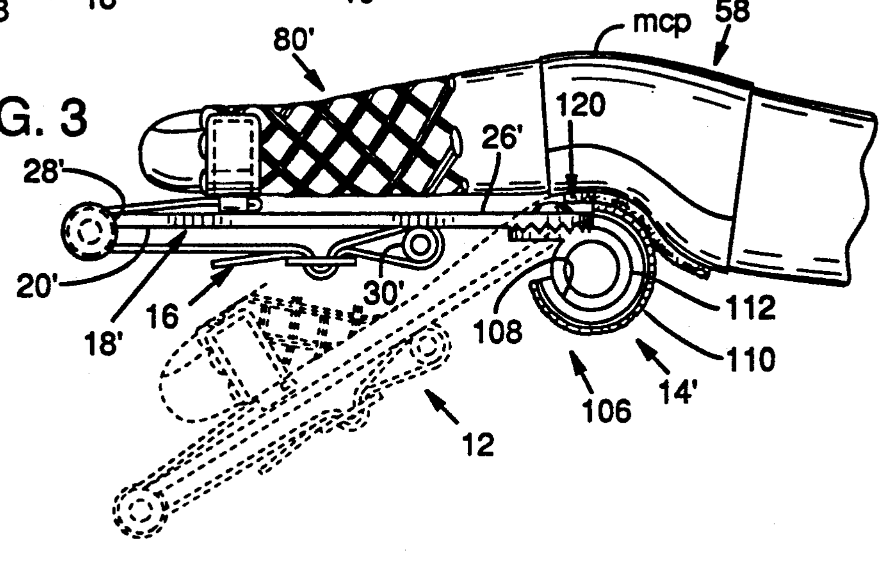
FIG. 3 is a view similar to FIG. 1 of a second embodiment of the invention.

FIG. 5 illustrates a second embodiment 12 of traction frame or plate which is included in the system shown in FIG. 3.

The system of FIGS. 1 and 2 and the system of FIG. 3 share similar arrangements for anchoring to the hand (anchoring arrangements 14, 14') and for transmitting traction to the digit (one or more traction transmission subassemblies 16).

The digital traction system will now be described in more detail with particular reference to the first embodiment and FIGS. 1, 2 and 4. The traction plate or frame 18 is a frame-like member, having a body 20 preferably made of a relatively thin and stiff, flat piece of suitable material such as plastic. In this embodiment the generally laminar traction plate is mounted onto the palmar side of the hand. The body 20, trapezoidal in shape, has opposite surfaces, digit side 22 and tensor side 24. The parallel sides of the trapezoid comprise the shorter inner anchor end 26 and the longer, outer tensor return end 28. As seen clearly in FIGS. 1 and 2, the traction plate body 20 is dimensioned so that the inner end 26 approximately matches the width of the palm p of the hand, the outer end 28 accommodates a comfortable spread of the fingers f of the hand, and the plate is of a length sufficient to extend somewhat beyond the fingertips ft.

A cleat bar 30, preferably of circular cross-section and with a smooth low friction surface, extends transversely on the tensor side 24 of the traction plate body 20. The cleat bar 30 overlays and approximately bisects a series of cleat slots 32 extending transversely across the body 20. In the present embodiment, one end of the cleat bar 30 carries a tensor holding loop or ring 34 (see FIG. 2). This holding element, ring 34, may be threaded into the end of the cleat bar 30 so that it may be optionally mounted on either end of the cleat bar. It may also be in the form of a hook or other suitable retaining shape and may be integral with the cleat bar 30 or mounted by any other suitable means at or adjacent the end of the cleat bar 30

The inner end 26 of the traction plate 18 carries an anchor cylinder 36 which extends the full width of the anchor end 26 of the traction plate 18 and is preferably integral with the plate and offset towards its tensor side 24. A patch 38 of hook and loop type fastener fabric extends the full length of the anchor cylinder 36 and covers about half its circumference, centered generally towards the digit side 22 of the traction plate body 20.

The outer end 28 of the traction plate body 20 carries a series of three spaced apart coaxial bushings, end bushings 40 and an intermediate bushing 42. The bushings 40, 42 are preferably offset somewhat towards the tensor side 24 of the traction plate body 20 (FIG. 1). A long bolt 46 with a flat knurled head 48 extends through the bushings 40, 42 and journals a pair of tubular rollers 50, captive between the bushings. A traction plate extender 52 is threaded onto the end of the bolt 46 and serves both to retain the bolt and to provide a positioning groove 54 for a tensor member (to be described below), the groove being defined in part by an inclined inner shoulder 56.

In the anchoring arrangement 14 of this first embodiment (FIGS. 1, 2 and 4) the base member is a fingerless glove-like member 58. As seen clearly in FIG. 4 the glove-like anchoring member 58 may embrace only the four fingers of the hand and be only long enough to accommodate a rectangular patch 60 of hook and loop fastener fabric such as that sold under the trademark "VELCRO" and include crotch elements 62 for engaging the crotches fc between the fingers. Preferably the glove-like member 58 is stretchable to fit a range of hand sizes and may, for example, be of a construction used in many athletic gloves and including a palm member 64 of relatively thin leather and a back 66 of a stretch fabric. Important characteristics of the anchoring member 58 are that, in use, it bears on and partially conforms to at least part of the hand and includes a portion engageable with at least one of the crotches between the fingers.

The anchoring arrangement 14 is completed by the contoured anchor member, anchor end cylinder 36 of the traction plate 18. In assembly, and as seen best in FIG. 1 the hook and loop fastener fabric patches 38, 60 register and are adjustably engageable so as to fix substantially the position of the traction plate 18 relative to the hand.

Each traction transmission arrangement 16 includes a tension member, a thin narrow elastic band or tensor 68 formed in a loop 70 around the cleat bar 30 and adjustably secured by a slide fastener 72. The elastic band/tensor 68 passes over one of the rollers 50 and returns (74) on the digit side 22 of the traction plate body 20 for attachment to a finger f. (For thumb traction in this first embodiment the tensor 68 is trained over the groove 54 of the traction plate extender 52).

In these exemplary embodiments traction is ultimately applied to the digit by a finger trap 80 which, for gripping the digit, uses the principle of the well known so-called Chinese finger trap. The body or sleeve portion 82 of the finger trap is formed from braided strands forming a sleeve which, when relaxed, slides easily onto the digit. When the outer ends of the strands are grasped attempts to withdraw the finger are defeated by the sleeve 82 contracting and gripping the finger. In this exemplary embodiment, attachment of the elastic band/tensor member 68 to the finger trap 80 is made by securing the tensor 68 into a slotted catch 84 fixed to a flexible connection plate or patch 86. Preferably the connecting element or catch 84 is disposed so that, in assembly, it is inset from the end of the sleeve 82. Connection patch 86 at least partially wraps and is fixed to, by some suitable method such as stitching 88, the outer end of the finger trap sleeve 82.

Looking in more detail at the construction of the sleeve 82 of the finger trap 80 illustrated in FIGS. 1–3—the basic element of the sleeve is a pliable filament 90, a plurality of which are bundled loosely into each strand 92. Polypropylene is a preferred material for the filaments 90. Preferably, in each strand 92, the filaments 90 lie loosely together substantially linearly (they are not twisted, in rope fashion). The strands 92 are conventionally braided together to produce an open center sleeve or tube 82 which, when extended axially, contracts in diameter (similar to a Chinese finger trap). The braiding defines right-and left-hand spiral strands 92*a*, 92*b* respectively. The ends of the sleeve 82 are formed or terminated by bonding or cementing together at joints or nodes 94, pairs of strands consisting of one right hand and one left hand strand 92*a*, 92*b* at their crossover points. Preferably all the filaments of each strand are captured at each bonded joint 94. It is noted that this form of sleeve 82 is similar to that which would be obtained from a suitable "off-the-shelf" hollow-braided rope, cut to length at suitable points related to the braid pattern, and with the strand ends secured as described above. In another form (not shown in the drawings) the braid may be formed with the "connecting" left and right hand strands being continuous so that at one end of the sleeve the terminations are in loops rather than in jointed nodes (94).

A particular configuration of braiding has been found to be advantageous for use in the traction system of the invention and is illustrated in FIGS. 6 and 7. Each strand of a given right or left-hand spiral 92*a*′, 92*b*′ successively passes over and under, sequentially, pairs of strands rather than single strands of the opposite spiral. This basic configuration of braiding, particularly when made from finer and more closely woven filaments, has been found to be particularly comfortable and efficient in applying traction to a digit. Good results have been obtained using commercially available braided electrical sleeving such as that sold under the trademark EXPANDO by BentleyHarris (Bentley-Harris Mfg. Co., 241 Welsh Pool Road, Lionville, Pa. 19353). For best results the open ends of the sleeve 82′ must be "set" to prevent their unraveling, for example by coating the strands with an adhesive for some significant length of the end portion of the sleeve (96*a*, 96*b*). Mounting and dismounting of the sleeve onto and from the digit is facilitated by flaring the proximal end 98 before coating the strands as shown in FIG. 6.

The finger trap connecting patch or plate 86 may be made of a suitable, thin, flexible material such as nylon. The stitching 88 of the connecting patch 86 to the strands 92 of the sleeve may also be of nylon. The stitching 88 should embrace a substantial number of the filaments 90 of the strands 92 which it wraps so as to be firmly anchored to the strands and positively transmit an applied traction force into the sleeve as a whole. For the more coarsely woven finger traps shown in FIGS. 1–3 a connecting patch 86 which wraps the end of the sleeve 82 by at least more than half its circumference is preferred. In part, this arrangement distributes the traction force sufficiently uniformly into the strands 92 of the sleeve 82. At the same time this incomplete encirclement allows the connecting end 102 of the sleeve to adjust in diameter as required, along with the sleeve as a whole, to accommodate a particular finger size. The adhesive coating of the connecting end 102′ of the finger trap embodiment of FIGS. 6 and 7 permits a satisfactory connection to be made with a connecting patch 86′ of smaller arcuate extent.

The second embodiment of traction plate arrangement 12 shown in FIGS. 3 and 5 provides the same essential function as that of the corresponding traction plate 18 shown in FIGS. 1 and 2. But here the structure is modified so that each digit may have its own traction plate and so that traction plates are laterally adjustable with respect to the hand. The general form of the traction plate 18′ is similar to that of the first embodiment and includes a traction plate body 20′ carrying a cleat bar 30′ and a tensor return roller 50′ at its outer end 28′. Anchoring of the individual traction plate 18′ to the glove-like anchoring member 58 is by means of a generally cylindrical adapter 106 having an open groove or slot 108. The entire outer surface of the adapter 106 is covered with hook and loop fastener fabric 110. The individual traction plate 18′ carries at its inner anchor end 26′ an offset hollow boss or cylinder 112 which is sized to slidably engage the groove or slot 108 of the adapter 106. Thus a laterally adjustable connection is made. The arrangements of FIGS. 1 and 3 are generally similar except for the presence of the adapter cylinder 106 between the traction plate and the glove-like anchoring member.

A "rosette" connection 120 between the traction plate 18' and the cylinder 112 permits swiveling or pivoting adjustment of the plate 18' relative to the adapter 106 and hence to the hand. The lateral position of a plate may be adjustably "stopped" by selective use of spacers 114 slidable in the adapter, preferably in conjunction with a fixed end stop such as cap 116.

Turning now to the assembly and mounting of the invention and with particular reference to FIGS. 1, 2 and 4—assembly may begin by pulling the fingerless glove-like anchoring member 58 onto the hand h (right hand is assumed) so that the crotch members 62 of the glove-like member are positioned snugly against the finger crotches fc. This places the fastener pad 60 in the palm of the hand and close to the base of the digits and hence metacarpophalangeal joints (mcp). A glove-like member embracing only the four fingers, as illustrated, is adequate for its purpose. Absence of the thumb makes the glove-like member easier to mount and suitable for both left and right-hand use. However a longer glove with a thumb member may be used if desired.

Next the traction plate 18 and the traction transmission member 16 may be assembled together as in the configuration shown in FIGS. 1 and 2 with the slide fasteners 72 of the tensor bands 68 used to set the length of the tensors in anticipation of the degree of traction to be applied. Then the finger traps 80 may be slid onto each digit. Only one reference numeral 80 has been applied to the finger traps shown in FIGS. 1 and 2 but in fact they may be of varying sizes to suit the typical range of finger sizes found in the human hand.

Limited use of the hand is possible when the traction plate arrangement of FIGS. 3 and 5 encumbers only one or two digits. With both embodiments all of the fingers may be flexed at the same time through a substantial portion of the normal range of motion of the mcp joint.

The particular sleeve (82, 82') construction and choice of materials also contribute to superior finger trap performance and comfort. The sleeve retains its resilience and a high coefficient of restitution to its original relaxed form even after many uses so that it can continue to grip the digit readily and consistently. A relatively loose arrangement of the filaments 90, 90' within the strands 92, 92' allows the strands to spread on contact with the digit, conforming to its surface, bringing many filaments into contact with the digit and so spreading the load for a comfortable but reliable grip.

An object of the present invention is to provide a particularly light and compact traction device. In keeping with this object a finger trap 80, 80' having a sleeve member 82, 82' open at the tip or connecting end 102, 102' and providing a connection point (catch 84, 84' on connecting patch 86, 86') inset from the end of the sleeve permits making the connection of the tensor 68, relative to the finger, at a point substantially inset from the finger tip ft. Thus, the traction plate 18 need not extend substantially beyond the fingertip, if at all, but may still provide sufficient longitudinal space for a functionally adequate length (74) of tensor on the digit side 22 of the traction plate. Thus compactness in terms of traction plate length is achieved. Clearly, provision of a "return configuration" (rollers 50) for the tensors 68 also contributes to compactness. The same length of tensor 68 stretched on only one side of the traction plate would require a much longer traction plate. However, although less compact, such a traction plate and tensor configuration could be used satisfactorily with the anchoring arrangements and finger attachment of the invention.

With the digits engaged by the finger traps 80 and the tensors 68 trained around the rollers 50, the traction plate 18 may be brought into position alongside the palmar side of the fingers. The hook or loop pad 38 on the anchor end cylinder 36 of the traction plate ma then be brought into engagement with the mating pad 60 on the glove-like member 58 in a position comfortable for the patient and anchoring the traction device close to the base of the digits or mcp joints to be treated. As seen clearly in FIG. 1 there is only limited arcuate engagement between the mating pads 38, 60, at what may be termed a localised anchoring area, adjacent the mcp joints. Typically this mounting sequence will have placed an initial tension in the tensors 68. Final tension may be set as required using the slide fasteners 72 for adjustment. The separable nature of the two components (anchoring end of the traction plate 18, glove-like member 58) of the anchoring arrangement provides some basic adjustment of the fit or relative longitudinal and lateral positions of the traction plate 18. The overlapping extent of the hook and loop fastener patches or pads 38, 60 provides this latitude.

In an alternative method, the traction plate 18 and glove-like member 58 may be mounted onto the hand first. Then each finger trap 80 may be mounted onto its corresponding finger after training its tensor 68 around the roller 50.

The mode of application shown in FIGS. 1 and 2 and whose method of mounting has just been described, is an inside or palmar embodiment of the invention with respect to the positioning of the traction plate 18. In this mode the digits are significantly immobilized, although some limited flexing of the interphalangeal joints in the direction of closing the hand is feasible, and, of course, the mcp joints are unencumbered and free to articulate. In this mode, however, the thumb is relatively free to articulate as the use of the traction plate extender 52 does not require that the traction plate underly the thumb as it does the fingers.

Essentials of the tension members or tensors 68 is that they be elastic, suitably flexible, and that they have a "spring rate" suitable to the application and, preferably, that the spring rate is maintained in prolonged and repeated use of the device.

Clearly for consistent application of the desired traction to the digit the outer end 28 of the traction plate body 20 must provide a "tension member return surface" offering little frictional resistance to relative movement of the tensor 68 where it reverses direction or returns to connect with the finger trap 80. The exemplary preferred embodiment uses freely rotating rollers 5 but other arrangements are possible given suitable material selection, both for the traction plate body 20 and the tensor 68, such as a smooth rounded edge or bead at the outer end 28, integral with the traction plate body 20. Provision of the inclined shoulder face 56 on the traction plate extender 52 helps to minimize friction in the thumb tensor if the application configuration results in a side load at this contact point. If thumb traction is not indicated, the traction plate extender 52 may be replaced by a simple cap nut (not shown in the drawings). Elastic cords are shown as an exemplary embodiment of tensor 68. The tensor or tension member could, of course, take other forms such as a combination of extension spring and inelastic cord.

One size of traction plate 18 may fit a range of hand sizes, in part due to the provision of extra slots 32 offering a choice of lateral spacing for anchoring the tensors 68. The trapezoidal shape of the traction plate provides a wider outer end 28 so that the tensors 68 may be splayed or fanned out as required to match the particular digital spread of an application.

The traction plate 18 is symmetrical about longitudinal center line so that it may be used equally on either the left or right-hand. On either hand, the digit side 22 of the plate is towards the palm. If they are detachable, the traction plate extender 52 and the cleat bar loop o ring 34 (both for the thumb), may both be relocated on the opposite side of the traction plate as required. Or, as suggested above, a permanent anchor point for the thumb tensor may be provided at both sides of the traction plate in place of the removable ring 34.

The general mode of operation and application of the second embodiment of traction plate arrangement shown in FIGS. 3 and 5 is as just described. But an advantage of this second arrangement is that it provides for installing only as many traction plates 18' as are needed. Thus, if only one or two digits are to be treated the remaining digits are unencumbered. As indicated in FIG. 3 individual traction plates 18' may rotate or hinge within the anchor cylinder 106. This permits independent flexing of individual digits and may extend the range of articulation of the mcp joints while under treatment. Traction plates 18' may slide laterally within the anchor cylinder 106 and be positioned to best suit the digit being treated making selective use of spacers 114 which may be of different length. A swivel connection, such as rosette 120, provides further adjustment. A traction plate 18' may be angled towards the radius or ulnar sides of the hand to deviate the traction force from the axial so as to counteract radial or ulnar drifts respectively of the mcp joints. Even when only one or two digits are being treated the anchor cylinder 106, extending the full width of the palm of the hand, provides a stable and secure base of attachment for the traction plates(s) 18'.

A digital traction system according to the invention is simple, light and compact with a potentially low cost of manufacture. Components of a single size may comfortably accommodate a wide range of hand sizes. Assembly or reassembly to establish desired mode of operation or to prepare for left or right handed use may easily be done by the patient or others without special tools or equipment. Independent adjustment of degree of traction for each digit is also simply made and may be controlled by the patient if desired.

An advantage of systems according to the invention is that, as is clear from the drawings and above description, a traction plate or frame is anchored to the extremity solely by attachment or anchoring adjacent to the metacarpophalangeal joints (in the hand application). But the traction plate remains substantially free of the digits and all of the interphalangeal joints are substantially unencumbered by the anchoring means and at least partially free to articulate while under traction, so that the system may be termed a dynamic traction system. In particular the effective anchoring point may clearly be so close to the metacarpophalangeal joint as to permit that joint to be articulated through at least a substantial part of its normal range of motion while under traction (as indicated in FIG. 3). In using the system the mcp joint or joints are, of course, always subject to traction as transmitted through a digit. The degree to which the proximal and distal interphalangeal joints are "loaded" may be varied according to the means and location of connecting the tension member (68) to the digit.

The invention is enhanced by a particular construction and configuration of finger trap which contributes to the compactness and efficiency of the system while adding to patient comfort.

Those of ordinary skill in the art will recognize useful variation of the embodiments and modes of application described above falling within the scope of the invention and intended to be embraced by the claims which follow.

I claim:

1. A traction system for applying traction to at least one of the metacarpophalangeal joints (mcp) of a hand, the hand having a plurality of digits (f) and crotches (fc) between the digits, the system including a traction frame (18, 18') for anchoring alongside the hand and means (16) connectable between at least one digit and the frame for applying an axial traction force through the digit to the corresponding metacarpophalangeal joint characterized in that the system includes a glove-like anchoring member (58) embracing and covering at least part of the hand in a substantially fixed relationship with the hand and in that the traction frame (18, 18') is anchored to the hand by means of connection to the anchoring member (58) and in that the means (16) for applying a traction force comprises an elongated flexible element having first and second opposite ends and including an elastic portion, the first end being connectable to the at least one digit and the second end being connectable directly to the frame, and so that, in use, retraction of the traction frame under the action of the traction force applying means (16) is resisted substantially by the engagement of the anchoring member (58) with the hand.

2. The traction system of claim 1 wherein the anchoring member (58) provides the sole means for anchoring the traction frame (18, 18') to the hand and the traction frame provides the sole means for connecting the second end of the elongated flexible element.

3. The traction system of claim 1 wherein the traction frame (18, 18') is anchored to the hand by the anchoring member (58) at the palm (p) of the hand, at a localised anchoring area adjacent the metacarpophalangeal joints (mcp).

4. The traction system of claim 1 wherein the traction frame (18, 18') is releasably connected to the anchoring member (58).

5. The traction system of claim 1 including means (38, 60; 108, 112; 120) for providing lateral adjustment of at least a portion of the traction frame (18, 18') relative to the anchoring member (58).

6. The traction system of claim 1 wherein the traction frame (18') accommodates only a single digit (f) of the hand.

7. The traction system of claim 1 wherein the traction frame (18, 18') includes a laterally extending contoured surface (36, 106) for engaging the anchoring member (58).

8. The traction system of claim 7 wherein the engagement of the laterally extending contoured surface (36, 106) with the anchoring member (58) provides for an adjustable point of attachment of the traction frame (18, 18') to the hand.

9. The traction system of claim 8 wherein the contoured surface (36, 106) of the traction frame and the anchoring member (58) each carry patches (38, 110) of hook and loop type fastener fabric and, in use, said patches are brought into register for anchoring engagement of one with the other.

10. The traction system of claim 1 wherein the anchoring member (58) embraces at least two adjacent digits of the plurality of digits and engages the crotch (fc) between the adjacent digits (f) so that, in use, retraction of the traction frame (18, 18') under the action of the traction force applying means (16), may be resisted at least partially by the engagement of the anchoring member with said crotch.

11. The traction system of claim 1 wherein the anchoring member (58) includes a digit embracing portion embracing only a proximal portion of the at least one of the digits (f), leaving a distal portion exposed, for facilitating connection of the traction force applying means (16).

12. The traction system of claim 1 wherein the means (16) connectable between the at least one digit (f and the traction frame (18, 18') for applying a traction force includes a finger trap sleeve (80, 80') engaging the digit, said sleeve, upon the application of a tensile force, contracting in diameter so as to grip the digit.

13. A finger trap (80') for use in applying traction to a digit (f) of a human extremity, the trap having distal and proximal ends and being of the type which contracts to grip the digit upon the application of a traction force in the direction of the distal end of the trap, characterized in that the trap (80') comprises an elongated braided sleeve (82') having opposite ends (98, 102') and being open at both ends, the sleeve including a plurality of strands (92), the strands being forced into respective left (**92*b*) and right-hand (92*a*) spirals, each strand being an element of the braid and comprising a bundle of individual filaments (90), wherein the configuration of the braid of the sleeve is such that each strand of a given right or left-hand spiral successively passes, sequentially, over at least two of the strands (92) of the opposite spiral and then under at least two strands of said spiral and the sleeve carries a connecting element including means (84) for connecting to a tension member (68,74) for applying the traction force, the connecting element being carried by the sleeve (82'**) intermediate its opposite ends and making force transmitting connection with a plurality of the strands.

14. A finger trap for use in applying traction to a digit of a human extremity, the trap having distal and proximal ends and being of the type which contracts to grip the digit upon the application of an axial traction force, characterized in that the trap comprises an elongated braided sleeve having opposite distal and proximal ends, at least the proximal end being open, and including a plurality of strands, the strands being formed into respective left and right-hand spirals, each strand being an element of the braid and comprising a bundle of individual filaments, wherein the configuration of the braid of the sleeve is such that each strand of a given right or left-hand spiral successively passes, sequentially, over at least two of the strands of the opposite spiral and then under at least two of the strands of said opposite spiral and the sleeve carries a connecting element including means for facilitating the application of the axial traction force, the connecting element being carried by the sleeve intermediate its opposite ends and making force transmitting connection with a plurality of the strands.

15. The finger trap of claim 14 wherein both of the opposite ends of the sleeve are open.

16. The finger trap of claim 14 wherein the open proximal end of the sleeve is set in a flared configuration to facilitate mounting the sleeve onto a digit.

17. The finger trap of claim 14 wherein the connecting element is disposed towards the distal end of the sleeve.

* * * * *